United States Patent [19]

Drewlow

[11] Patent Number: Plant 6,394

[45] Date of Patent: Nov. 15, 1988

[54] STREPTOCARPUS PLANT NAMED MINERVA

[75] Inventor: Lyndon W. Drewlow, Ashtabula, Ohio

[73] Assignee: Mikkelsens, Inc., Ashtabula, Ohio

[21] Appl. No.: 9,374

[22] Filed: Jan. 30, 1987

[51] Int. Cl.[4] ..... A01H 5/00
[52] U.S. Cl. ..... Plt./68
[58] Field of Search ..... Plt./68

*Primary Examiner*—Robert E. Bagwill
*Attorney, Agent, or Firm*—Schwartz, Jeffery, Schwaab, Mack, Blumenthal & Evans

[57] ABSTRACT

A Streptocarpus plant named Minerva characterized by its numerous short leaves in rosette form, blue violet flower color, floriferous habit, compact growth habit, early flowering and ability to flower under low light levels and high temperatures, and by its long lasting and non-shattering flowers.

1 Drawing Sheet

The present invention relates to a new and distinct cultivar of Streptocarpus plant, botanically known as *Streptocarpus×hybridus,* and known by the cultivar name Minerva. Minerva was developed by me through controlled breeding by crossing Thor (seed parent)-×Neptune (pollen parent). Neither parent cultivar is patented.

Asexual reproduction by leaf cuttings has shown that the unique features of this new Streptocarpus are stabilized and are reproduced true to type in successive propagations.

The following characteristics distinguish the new Streptocarpus from both its parent varieties and other cultivated Streptocarpus of this type known and used in the floriculture industry:

1. Minerva is characterized by numerous short leaves in the form of a rosette instead of one large leaf that characterizes many older Streptocarpus cultivars. This results in a cluster of flowers in the middle of green foliage making an attractive 10 cm flowering plant.

2. From a well rooted plant out of a 72 cell pack a well developed flowering plant is obtained in 6 to 10 weeks making it earlier than Neptune and Thor.

3. Minerva is deeper blue in flower color and has less yellow color in the throat than Neptune, and does not have as much violet color as Thor. The flower color is a darker blue than both Orion and Janus, the cultivars being disclosed in pending applications.

4. Growth habit of Minerva is similar to Neptune, Thor, and Pegasus (patent applied for) and more compact than Janus and Orion.

5. The leaves on Minerva are not as coarse and brittle as Thor and Neptune but similar to Pegasus, resulting in a plant that is easy to ship.

6. Minerva is superior in plantlet formation from leaf cuttings to Thor and Neptune. It is similar to Electra (patent applied for) but not as good as Orion and Janus. Plantlets form in eight to ten weeks depending on the season of the year.

7. Flowers on Minerva are larger and not as cupped as Neptune; are similar in size to Thor but not as cupped, and are not as large as Ariadne (patent applied for) and Ulyssus (patent applied for).

8. Minerva has demonstrated the ability to tolerate overhead watering with colder than normal water (40° F.) without foliar spotting, and tolerates fairly high light levels in summer without leaf yellow and bronzing which occur in both Thor and Neptune.

9. Minerva will flower both under the lower light levels of winter (December to February) and the high temperatures of summer (July to September) without ever going out of bloom under greenhouse conditions. Many older cultivars would not bloom under these conditions.

10. Minerva has numerous 40 to 45 mm flowers with up to 3 per stalk that are non-shattering and long lasting which results in an ideal flowering pot plant.

The accompanying color photograph illustrates in perspective view the overall appearance of Minerva, with colors being as true as reasonably possible in a color reproduction of this type.

The following is a detailed description of my new Streptocarpus cultivar based on plants produced under commercial practices in Greenhouses of Mikkelsens Inc., Ashtabula, Ohio. Color references are made to The Royal Horticultural Society Colour Chart (RHS), except where general colors of ordinary dictionary significance are used.

Classification:

*Botanical.—Streptocarpus×hybridus,* cv. Minerva.

Parentage: Controlled cross of Thor×Neptune.

Propagation:

A. *Type cutting.*—Leaf.

B. *Time to develop plantlets.*—Summer: 8 weeks at 20° C.; Winter: 10 weeks at 20° C.

C. *Rooting habit.*—Numerous, fine, fibrous.

Plant description:

A. *Form.*—Leaves rosette from a crown at the soil line, with flower stalks forming at the leaf midrib. Many leaves in a symmetrical pattern.

B. *Habit of growth.*—Flowers carried along foliage. Vigorous, very free flowering, never going out of bloom once it starts blooming under greenhouse conditions.

C. *Height from soil line.*—10 to 12 cm.

D. *Spread.*—40 to 45 cm at maturity. Leaf Size: 18 to 24 cm in length and 7 to 8 cm in width at the widest point; leaf size can vary greatly with cultural conditions. Quantity: Mature plant may have more than 15 leaves. Leaf Shape: Elliptical. Texture: Lower surface rugose with veins protruding and pubescent — upper surface rugose and pubescent. Margin: Finely crenate. Color: Young foliage, top side 143A; under side 145B. Mature foliage, top side 137A; under side 146D. Ribs and veins: Pinnate. Rib and vein color: 146C. Leaf tips: Obtuse. Leaf base: Acute.

Flowering description: Flowers open one at a time on the individual flower stalks.

A. *Fully expanded.*—45 to 45 cm.

B. *Stem.*—Single, dark green with purple cast; long, slightly pubescent and round — several from a leaf midrib.

C. *Form.*—Funnel shaped in an umbel with upper two petals flexed and lower petals flattened to give an overall flat appearance.

D. *Flower bud description.*—20 to 25 mm at maturity, tubular with the end larger in diameter than the rest; 5 green calyx folded over the basal end.

E. *Flowers borne.*—In clusters of 2 to 3 flowers per flower stalk with 3 the most common, carried above foliate. Pedicels of the flowers in the inflorescence vary in length.

F. *Quantity of flowers.*—Mature plant can have more than 20 flower stalks open with up to 3 flowers per stalk.

G. *Permanence.*—Long lasting, 10 days or longer.

Color:

A. *Tonality from a distance.*—Dark blue with yellow and white in throat.

B. *Upper surface of petals.*—90B with 83B in the lower 3 petals.

C. *Under surface of petals.*—86C.

D. *Throat.*—1B streaks that fade to almost white as flower ages; 83B streaking, also some 91B in throat.

E. *Discoloration.*—Fading of older flowers to light blue with a more violet cast.

Petals:

A. *Texture.*—Satin.

B. *Appearance.*—Individually lobed with very slight crenate margins; top 2 petals reflexed and smaller than the 3 bottom petals which are flat.

C. *Arrangement.*—Regularly united into an almost circular shape.

D. *Persistence.*—10 days or longer. Remain on plant in dry form until picked.

E. *Fragrance.*—None.

Reproductive organs:

A. *Stamens.*—2 fertile. Anther shape: 2 fertile, interconnected and flat. Anther color: White, with purple cast. Filament: Attached to petals for 3 mm and free standing for 4 mm. Pollen color: White.

B. *Pistils.*—Stigma shape: 2 lobed flattened, rounded at end of lobes. Stigma color: White. Stigma size: 2 mm. Style color: White. Style size: 5 mm. Ovaries: Numerous, 12–14 mm on a receptive pistil, purplish.

Disease resistance: No disease problems to date.

Other important characteristics: Minerva's compact growth habit combined with its highly floriferous nature makes this cultivar suitable for 10 cm pot plant production. The long lasting, non-shattering flowers of Minerva and its pliable small leaves makes shipping easy. Its distinct dark blue color with less purple cast than other dark blue cultivars improves its appearance under fluorescent light. Lack of major disease and resistance to insects makes for a trouble free crop to grow.

I claim:

1. A new and distinct cultivar of Streptocarpus named Minerva, as illustrated and described, and particularly characterized by its numerous short leaves in rosette form, blue violet flower color, floriferous habit, compact growth habit, early flowering and ability to flower under low light levels and high temperatures, and by its long lasting and non-shattering flowers.

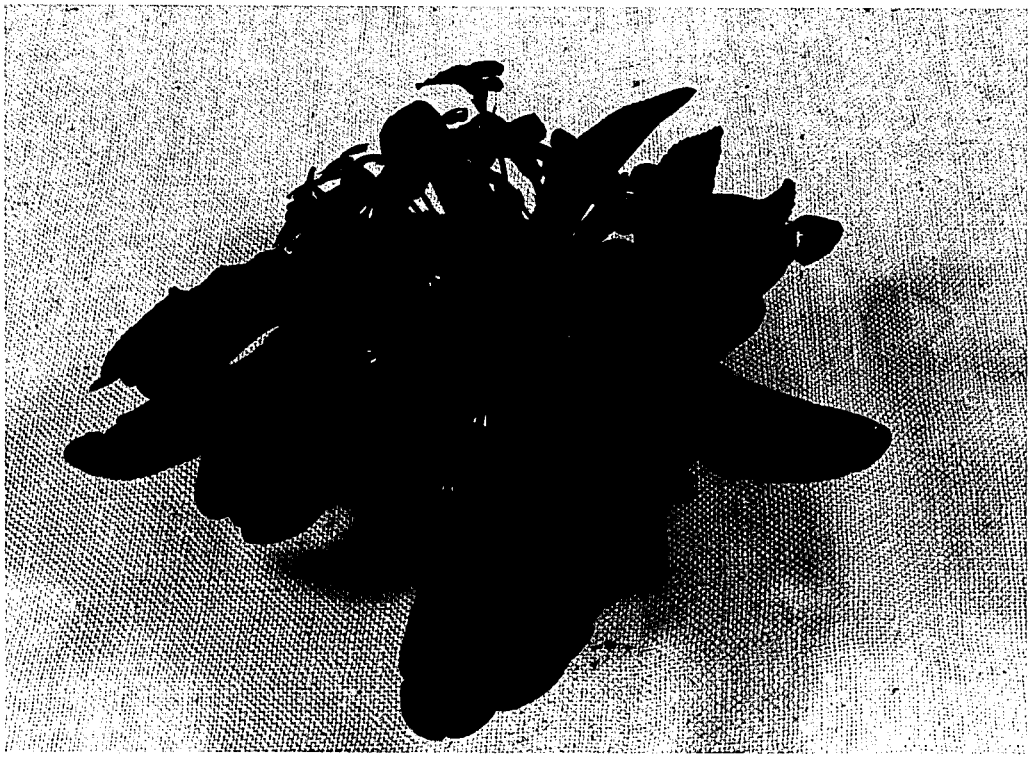

* * * * *